United States Patent [19]

McAleer et al.

[11] 4,110,223
[45] Aug. 29, 1978

[54] APPARATUS FOR RECOVERING EMBRYOS FROM EMBRYONATED EGGS

[75] Inventors: William J. McAleer, Ambler; William M. Hurni, North Wales, both of Pa.

[73] Assignee: Merck & Co., Inc., Rahway, N.J.

[21] Appl. No.: 744,228

[22] Filed: Nov. 23, 1976

Related U.S. Application Data

[63] Continuation of Ser. No. 572,584, Apr. 28, 1975, abandoned.

[51] Int. Cl.$^2$ .......................... B01D 33/22; A23J 1/09
[52] U.S. Cl. ...................................... 210/388; 195/1.8; 99/498
[58] Field of Search ................................. 99/495–498, 99/500; 210/388; 195/1, 1.3, 1.8, 127

[56] References Cited

U.S. PATENT DOCUMENTS

| | | | |
|---|---|---|---|
| 1,607,013 | 11/1926 | Meyerhofer | 210/388 |
| 2,382,492 | 8/1945 | Lomax | 210/388 |
| 3,651,846 | 3/1972 | Mirara | 99/498 |

Primary Examiner—Harvey C. Hornsby
Assistant Examiner—Robert Pous
Attorney, Agent, or Firm—Donald J. Perrella

[57] ABSTRACT

A method and apparatus for recovering embryos from embryonated eggs wherein the egg is cracked open the shell discarded and the contents dropped onto a continuously vibrating screen which separates the embryo from the yolk sac and accompanying fluid. This associated material, which is less cohesive than the embryo, passes through the screen. The screen itself is tilted at a compound angle from the horizontal and its vibrating action causes the embryos to move along the upper surface of the screen toward a discharge chute located at the lower corner of the screen.

11 Claims, 9 Drawing Figures

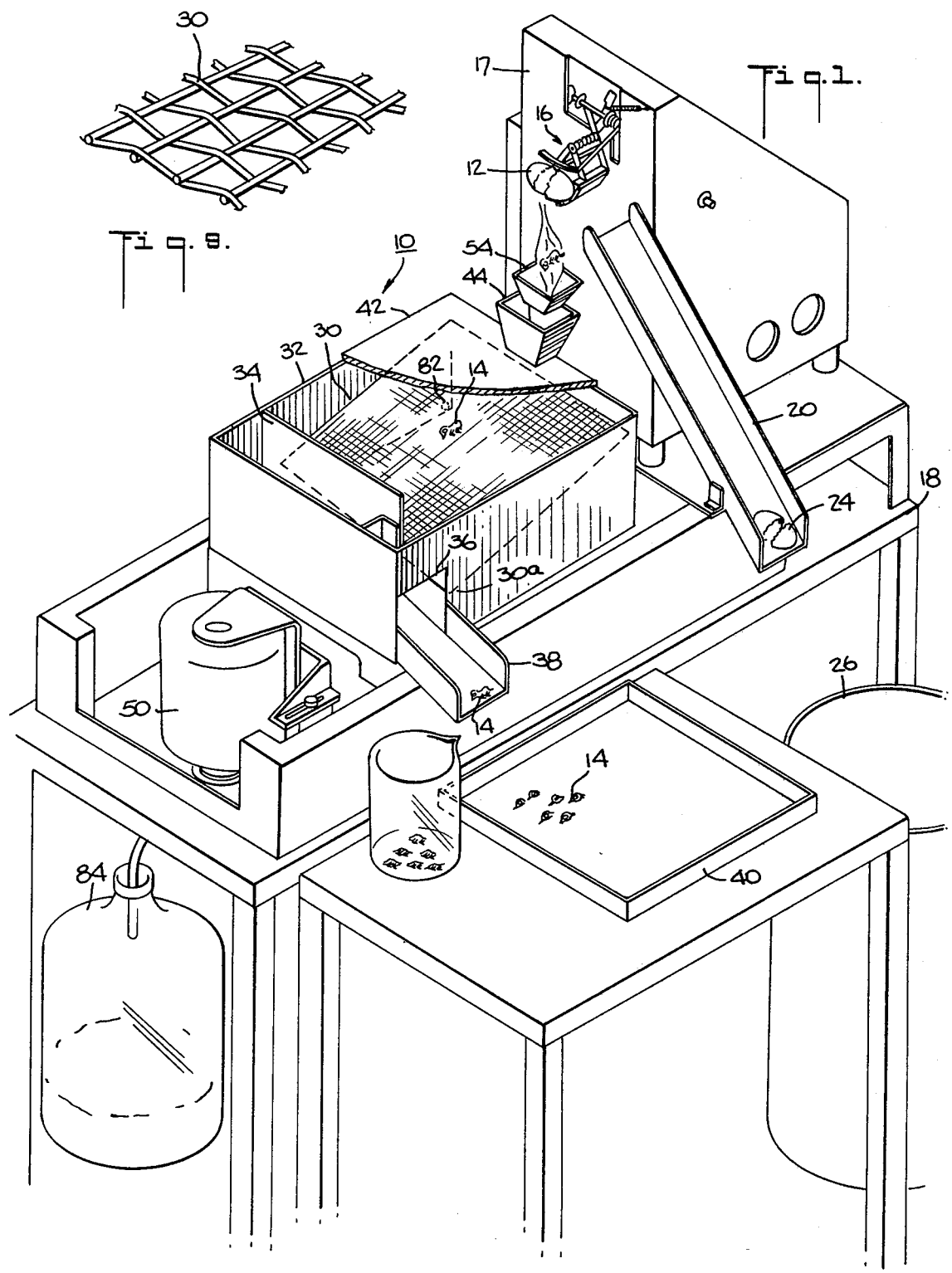

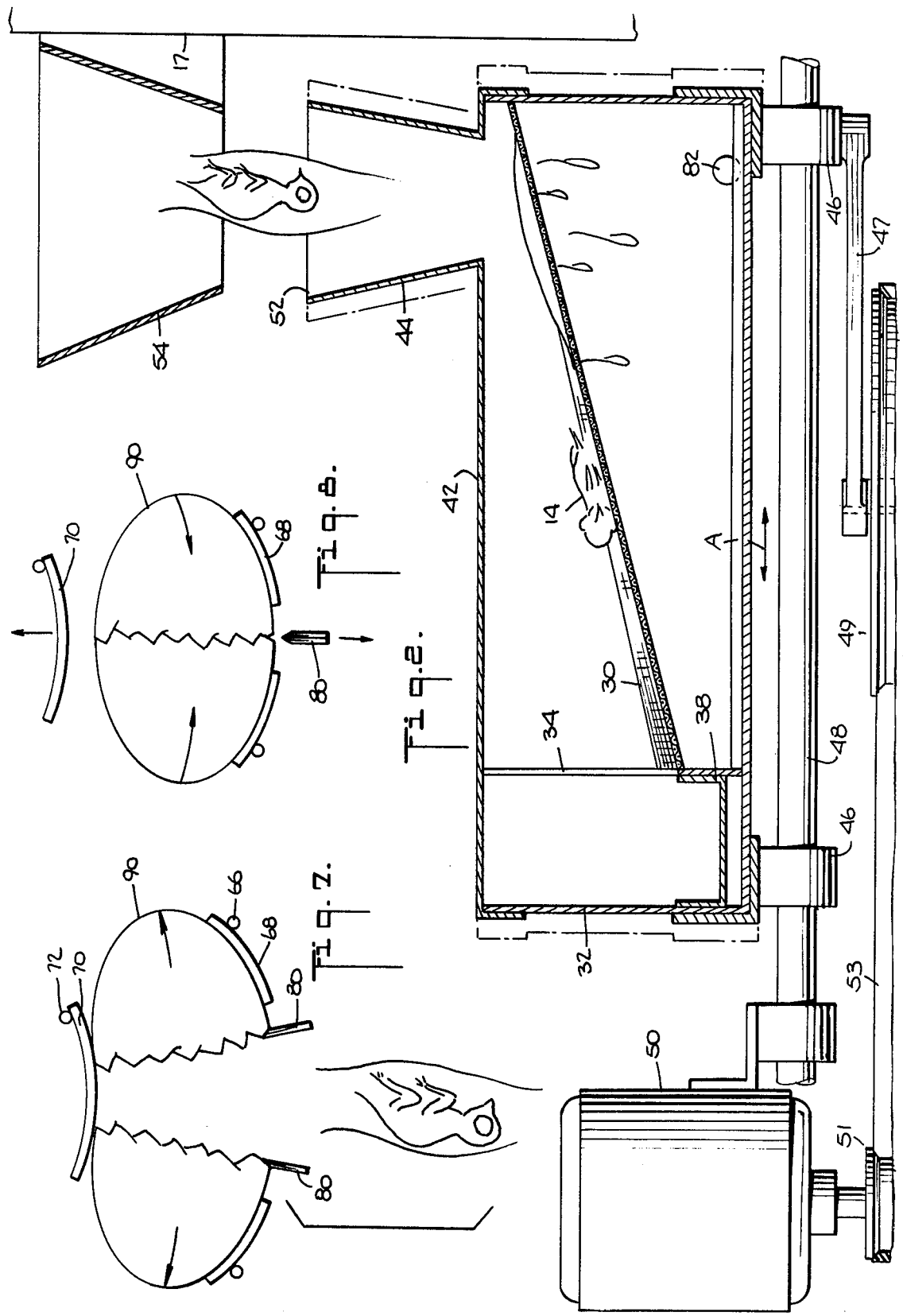

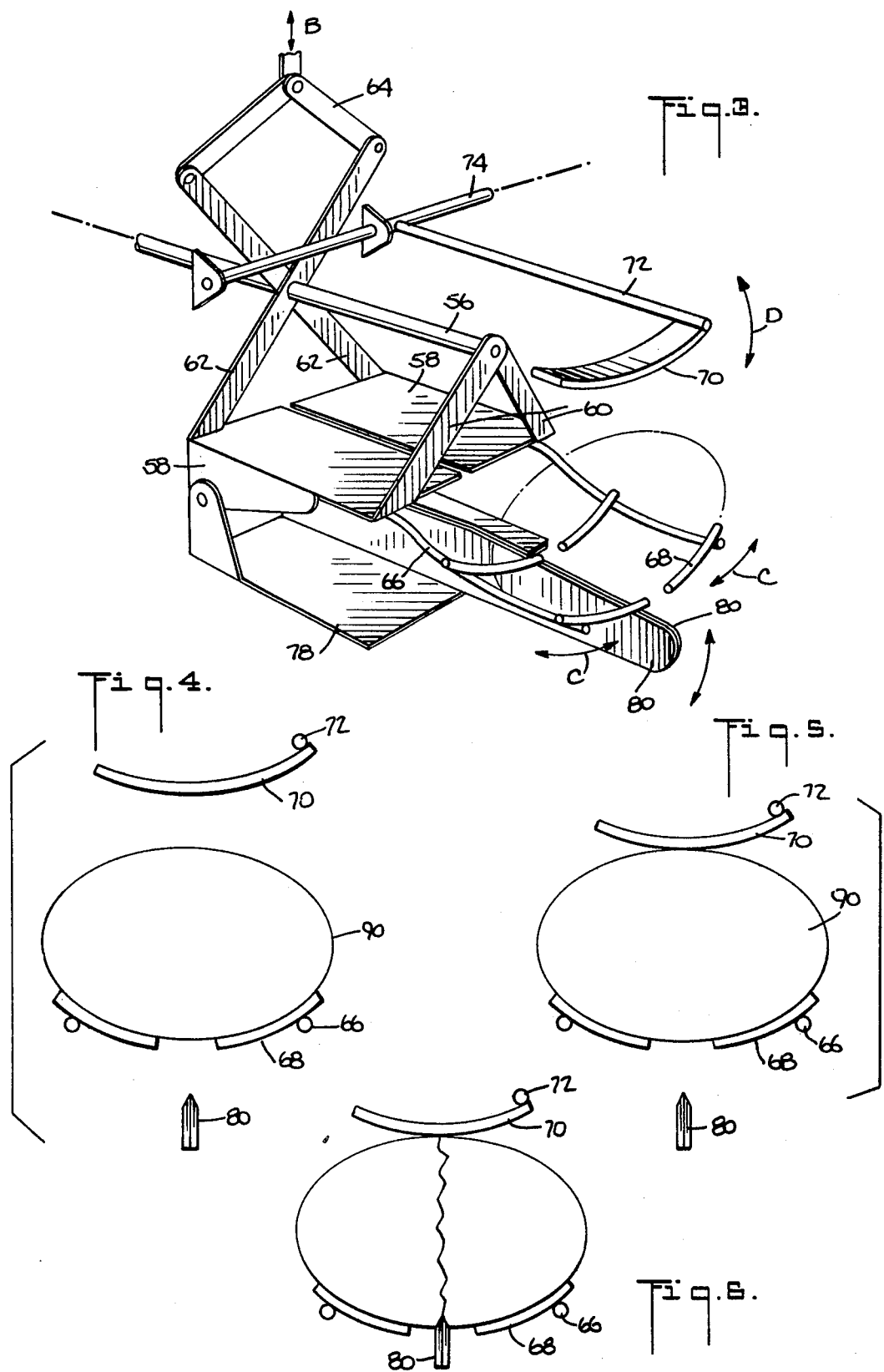

APPARATUS FOR RECOVERING EMBRYOS FROM EMBRYONATED EGGS

RELATED APPLICATION

This application is a continuation of application Ser. No. 572,584, filed Apr. 28, 1975, now abandoned.

BACKGROUND OF THE INVENTION

1. Field of the Invention

This invention relates to the recovery of embryos from embryonated eggs such as chicken or duck eggs, and more particularly it concerns novel techniques and apparatus for semi-automatically isolating embryos. The isolated embryos provide live tissue from which cells can be produced for various purposes such as the manufacture of vaccine.

2. Description of the Prior Art

Embryo recovery in the past has been an awkward and time consuming operation. In general, a manual method was used wherein an operator wiped the top of an embryonated egg with a gauze containing iodine and then with a gauze containing alcohol. A hand-held cracker was then used to break a circular area of shell which was then manually removed from the egg. The embryo contained within the egg was then removed by reaching into the egg with a pair of forceps and pulling the embryo out. The prior art method of retrieving embryos was employed due to the difficulty of selectively isolating the embryo from the egg. This required human intervention since the embryo and associated components are similar in nature, requiring a highly selective system to successfully retrieve them.

This prior art procedure presented several difficulties: (1) due to human handling throughout the operation, contamination is considerable, (2) this procedure does not permit the handling of large numbers of eggs and, (3) due to the time lag between embryo isolation and processing to produce cell slurry in the manual method, significant tissue degradation occurs with resultant reduction in cell yield.

SUMMARY OF THE INVENTION

The present invention avoids the above described disadvantages of the prior art and provides arrangements by which embryos may be recovered very quickly and efficiently from large numbers of eggs. Moreover the present invention reduces the susceptibility of embryos to contamination during the recovery operations since it is a closed system involving minimal human contact.

According to one aspect of the invention embryos are recovered from eggs by cracking the eggs open and dumping their contents onto a screen which is tilted at a compound angle, from horizontal and which is continuously vibrated or shaken. The egg contents, which include relatively tough membranous tissue surrounding the various egg components, including the embryo are subjected to a shock upon initial impact with the screen and this ruptures and opens the membranous tissue and frees the more liquid components plus the embryo itself. As the tilted screen continues to shake the embryo, the membranous tissue and the more liquid contents separate further, while the embryo gradually works its way down toward the lowermost corner from which it exits through a chute. The fluid, membranous tissue and other material however pass down through the openings of the screen during the shaking action and they are thereby separated from the embryo.

The system that has been evolved requires a delicate balance of a number of parameters to insure success. If these parameters are not correct, the embryo may not be successfully separated or it may be destroyed during the operation. It should also be understood that the system has been designed for rapid, continuous operation so that embryos can be continuously fed into the system and continuously retrieved for use.

According to a further aspect of the invention an egg cracking and opening mechanism is arranged above a screen and means are provided to subject the screen to continuous shaking action so that the more fluid portions of an egg whose contents are dumped onto the screen will pass through the screen while the more solid embryo portion of the egg contents are retained on the screen.

In the preferred embodiment the screen is tilted at a compound angle from the horizontal while the egg cracking and opening mechanism is positioned over the screen near its uppermost corner and the embryo discharge chute is positioned at the lowermost corner of the screen.

There has thus been outlined rather broadly the more important features of the invention in order that the detailed description thereof that follows may be better understood and in order that the present contribution to the art may be better appreciated. There are of course, additional features of the invention that will be described hereinafter and which will form the subject of the claims appended hereto. Those skilled in the art will appreciate that this invention may be utilized as a basis for designing other structures or methods for carrying out the several purposes of this invention. It is therefore important that the claims be regarded as including such equivalent constructions and methods as do not depart from the spirit and scope of the invention.

BRIEF DESCRIPTION OF THE DRAWINGS

One embodiment of the invention has been chosen for purposes of illustration and description, and is shown in the accompanying drawings forming a part of the specification, wherein:

FIG. 1 is a perspective view partially cut away, of an embryo recovery system in which the present invention is embodied;

FIG. 2 is a side elevation view, partially in section, of the embryo recovery system of FIG. 1;

FIG. 3 is a perspective view of part of an egg cracking and opening mechanism employed in the system of FIG. 1;

FIGS. 4–8 are outline views showing the operation of the egg cracking and opening mechanism of FIG. 3; and FIG. 9 is an enlarged fragmentary perspective view of a screen employed in the system of FIG. 1.

DETAILED DESCRIPTION OF THE PREFERRED EMBODIMENT

As shown in FIG. 1 an embryo recovery system 10, according to the present invention, is used to open embryonated eggs 12 and recover therefrom partially developed embryos 14. These embryos provide tissue material from which cell cultures may be developed.

The recovery system 10 includes an egg cracking and opening mechanism 16 which is mounted on a support and operating mechanism 17 above one end of a table 18. A chute 20 extends down from one side of the cracking and opening mechanisms to convey emptied shells 24 to a waste container 26, positioned near or under the table 18.

An embryo separation screen 30 is positioned under the egg cracking and opening mechanism 16 to receive the contents of the eggs 12 which are dumped thereon. The screen 30 is mounted inside a box-like receptacle 32 so that, as shown in FIGS. 1 and 2 it is tilted at a compound angle from horizontal. It will be noted that the screen 30 tilts diagonally as it extends away from the cracking and opening mechanism so that one corner 30a of the screen is lowermost in the receptacle 32. Even this corner however is a finite distance above the bottom of the receptacle 32. It will also be noted that the egg cracking and opening mechanism 16 is positioned over the screen 30 near its highest corner.

A partition 34 extends across the receptacle 32 along the edge of the screen furthest from the egg cracking and opening mechanism 16. This partition terminates short of the receptacle wall closest to the lowermost corner 30a of the screen and forms an embryo outlet opening 36. An embryo discharge chute 38 extends from the opening 36 to the exterior of the receptacle 32. A tray 40 or other embryo receiving means may be provided beneath the chute 38, to receive the embryos 14 which pass out through the chute as shown in FIG. 1.

A removable cover 42 is positioned over the box-like receptacle 32, and an inlet hopper 44 is formed in the cover under the egg cracking and opening mechanism 16.

As shown in FIG. 2 the box-like receptacle 32 is mounted on slides 46 which move slideably back and forth along horizontal guide rods 48. A motor 50 is mounted on the table 18 and is connected through an oscillatory mechanism to the box-like receptacle to drive it back and forth as indicated by arrow A in FIG. 2. A preferred oscillatory mechanism includes a crank arm 47, a wheel 49, a pulley 51 and a belt 53. The crank arm 47 is pivotally connected at one end to the box-like receptacle 32 and is eccentrically mounted at the other end to the wheel 49. The wheel is driven by the motor 50 by means of the pulley 51 and the belt 53.

The extent of oscillation or shaking of the box-like receptacle 32 is indicated by the dotted outline of the receptacle 32 as shown in FIG. 2. It will be noted that the inlet hopper 44 has an upper opening 52 sufficiently large in the direction of shaking to remain under the egg cracking and opening mechanism 16 at all times.

The embryo feed funnel 54 is attached to the support 17 just below the egg cracking and opening mechanism to help direct the contents dropped from eggs cracked and opened by the mechanism 16 directly down into the inlet hopper 44.

The egg cracking and opening device 16 is of conventional construction and is commercially available for the baking industry. Only so much of the mechanism will be described as is necessary to clarify its operation in conjunction with the remainder of the embryo recovery system. As can be seen in FIG. 3, there is provided a main pivot rod 56 which extends horizontally out from the support 17. A pair of upper horizontal plates 58 are supported under the rod 56 by means of forward and rearward brace arms 60 and 62, each of which is pivoted to the rod 56. The rearward brace arms 62 extend up beyond the rod 56 where they are pivotally connected to a toggle-like actuation linkage 64. As can be seen in FIG. 4, the actuating linkage moves up and down, as indicated by the arrow B to cause the upper horizontal plates 58 to move laterally toward and away from each other, as indicated by the arrows C, as the associated support arms 60 and 62 pivot about the rod 56.

A cradle-like egg support extends forwardly of the plates 58. This support is made up of curved, forward protruding wires 66, extending outwardly from each of the upper horizontal support plates 58, and short, curved lateral wires 68 soldered or welded to different locations along the forwardly protruding wires 66. An upper, convexly curved, guide strip 70 is mounted on a cantilever arm 72 which in turn extends from a pivot rod 74 mounted on the support 17. This pivot rod extends horizontally in a direction perpendicular to the support rod 56 so that the guide strip 70 may move up and down as indicated by the arrow D.

Lower horizontal support plates 78 are pivotally connected, respectively, to each of the upper horizontal support plates 58 to pivot about an axis parallel to the pivot axis of the guide strip 70. A pair of knife blades 80 are attached, respectively, to the lower horizontal support plates 78. As can be seen in FIG. 4, when the upper and lower horizontal support plates 58 and 78 are laterally together, the knife blades 80 lie against each other and function as a single blade.

In operation, the egg cracking and opening device 16 is actuated at the appropriate speed by means of the drive unit (not shown) located inside the support 17. The sequence of cracking and opening an egg by the mechanism of FIG. 3 is illustrated in the diagrammatical views of FIGS. 4-8. As shown in FIG. 4, an egg 90 is positioned on the rods 66 and 68 when the convexly curved guide strip 70 is in its uppermost position and the knife blades are in their lowermost position. Thereafter, as shown in FIG. 5, the guide strip 70 is lowered down onto the top of the egg to hold it securely on the rods 66 and 68. Thereafter, the blades 80 are caused to lower, then spring upward and break through the egg shell by a slight amount, as shown in FIG. 6, to crack the egg shell about its periphery. Thereafter, as shown in FIG. 7, the knife blades 80 and associated portions of the cradle support rods 66 and 68 move apart while the guide strip 70 maintains upper support on the two halves of the thus cracked egg shell. This allows the contents of the shell to drop downwardly out from it. The timing of the cracking and opening mechanism is arranged such that the shell halves are held apart for a sufficient length of time to allow the relatively viscous contents of the embryonated egg to drop out from them. Thereafter, as shown in FIG. 8, the plates 58 and 78 are moved back together along with the knife blades 80 to reclose the egg shell 90. The guide strip 70 and the knife blades 80 are then moved away from the shell so that it may be removed and replaced by a new egg to be cracked.

During the above-described egg cracking and opening operation, the motor 50 maintains the box-like receptacle 32 and the embryo separation screen 30 oscillating or shaking in a horizontal plane in the direction indicated by the arrow A. When the contents of an opened egg pass through the hopper 44 and down onto the screen 30, the impact serves to rupture at least some of the membrane tissue surrounding and associated with the embryo to free the more liquid components plus the embryo itself. A distance of between ten to twelve inches between the egg cracking and opening device and the screen will produce a sufficient impact for rupturing and opening the membranous tissue. Thereafter, this material and the embryo are subjected to continuous shaking while the entire mass of material moves down along the tilted separator screen 30 toward the opening 36 leading to the discharge chute 38. As can be seen in FIG. 2, this shaking movement of the screen causes the unwanted tissue and liquid components of the egg contents to pass through the screen openings and into the bottom of the receptacle 32. Meanwhile, the more solid embryo portion of the egg contents remains on top of the screen and eventually passes through the opening 36 and out from the discharge chute 38 onto the tray 40.

The material which has passed through the screen 30 may be pumped, by an aspirating pump (not shown) out through an opening 82 in the receptacle 32 and down to a disposal container 84.

FIG. 9 shows a section of screen 30 used to isolate the embryos. As shown, the screen is constructed by intertwining strands of wire, preferably of stainless steel, and having a wire diameter of 0.060 inches. The screen has from 1 ½ to 3 ½ inches per linear inch, preferably 2 or 3 inches per linear inch, depending on the type and/or age of the embryonated eggs being processed. Other equivalent screens can be made by drilling or punching equivalent openings in a metal or plastic plate or sheet.

EXAMPLE

An apparatus is assembled as described in the drawing with a rectangular screen having a length of 13 inches (the X direction) and a width of 12 inches (the Z direction). The screen is mounted so as to be at a compound angle with the horizontal. Using point 30a (FIG. 1) as a reference point, the screen is elevated 2 1/16 inches at the corner to the right, 1 inches at the corner to the rear and 2 13/16 inches at the diagonally opposite corner. This produces an angle of inclination of slightly over 9° in the X direction and slightly over 4½° in the Z direction. The screen is mounted so as to oscillate a distance of about 2 inches at a frequency of about 4 ½ cycles per second. The screen is formed of stainless steel wire 0.060 inches in diameter and the mesh is 2 or 3 per linear inch depending on the type of embryo to be processed. The remaining parts of the apparatus are assembled as shown.

The apparatus substantially completely separates the embryo from the accompanying matter from the egg and does so on a continuous basis for as long a period as is desired.

It is important to understand that the success of the separation is not simply due to screen mesh but is dependent on the following parameters which must be delicately balanced to insure satisfactory separation: (1) screen mesh, (2) wire size, (3) screen path length, (4) screen inclination angle in both the X and Z plane; and (5) frequency of oscillatory motion of the screen. However, having thus described the invention with particular reference to the preferred form thereof, it will be obvious to those skilled in the art to which the invention pertains that various changes and modifications may be made therein without departing from the spirit and scope of the invention as defined by the claims appended hereto.

What is claimed is:

1. Apparatus for recovering embryos from embryonated eggs comprising an egg cracking and opening mechanism operative to crack open an egg and release the contents thereof to a predetermined area of a flat screen positioned under the mechanism, the screen having an edge farthest from the egg cracking and opening mechanism and the screen being tilted at a compound angle from horizontal whereby one portion of the screen is uppermost and the diagonally opposite portion is lowermost, a partition extending along part of the edge of the screen furthest from the egg cracking and opening mechanism and terminating before the lowermost portion of the screen, the lowermost portion of the screen communicating with a tilted embryo discharge chute, means operative to produce continual shaking of the screen and in cooperation with the screen tilted at a compound angle from the horizontal to move the contents of the egg in a random path away from the predetermined area of the screen to the embryo discharge chute and to provide separation of the more fluid portions of the contents from the more solid embryo portion, said more fluid portion passing through said screen and said embryo portion passing down said screen to said embryo discharge chute.

2. Apparatus according to claim 1 wherein the partition has an opening near the lowermost corner communicating with the tilted embryo discharge chute.

3. Apparatus according to claim 1 wherein the screen is mounted in a box-like receptacle and wherein the means for shaking the screen comprises vibrator means connected to said receptacle.

4. Apparatus according to claim 3, wherein the receptacle is provided with a cover, said cover having a hopper extending upwardly therefrom and positioned under said egg cracking and opening mechanism.

5. Apparatus according to claim 4 wherein the upper end of the hopper is sufficiently large in the direction of shaking so that it is able to receive the contents at all times during shaking.

6. In an apparatus for recovering embryos from embryonated eggs comprising an egg cracking and opening mechanism operative to crack open an egg and release the contents thereof, a screen positioned under the mechanism to receive the contents of the egg, means operative to produce continual shaking of the screen in a generally horizontal plane to separate the more fluid portions of the contents of the egg from the more solid embryo portion and fluid discharge means below the screen for removing the fluid portions from the receptacle, the improvement wherein the screen is a planar screen with four corners, mounted with a box-like receptacle positioned under the mechanism, the planar screen tilted at a compound angle from the horizontal whereby each corner is at a different height within the receptacle, the uppermost and lowermost corners being diagonally opposite one another, the uppermost portion of the screen positioned under the egg cracking and opening mechanism, the lowermost portion of the planar screen abutting a partition within the receptacle and communicating with a tilted embryo discharge chute, said more fluid portion passing through said screen and said embryo portion passing down said screen in a random path to said embryo discharge chute.

7. Apparatus according to claim 6 wherein the receptacle is provided with a cover, the cover having a hopper extending upwardly therefrom and positioned under the egg cracking and opening mechanism.

8. Apparatus according to claim 7 wherein the upper end of the hopper is sufficiently large in the direction of shaking so that it is able to receive the contents at all times during shaking.

9. In an apparatus for recovering embryos from embryonated eggs, the apparatus comprising an egg cracking and opening mechanism operative to crack open an egg and dump the contents thereof out from the shell, a screen mounted within the receptacle for receiving the contents from the mechanism and through the hopper, means operative to produce continual shaking of the receptacle and screen to separate the more fluid portions of the contents from the more solid embryo portion and fluid discharge means below the screen for removing the fluid portions from the receptacle, the improvement wherein the screen is a planar screen having four corners, the planar screen tilted at a compound angle from the horizontal whereby each corner is at a different height within the receptacle, the uppermost and lowermost corners being diagonally opposite one another, the uppermost portion of the screen positioned under the egg cracking and opening mechanism, the receptacle having a partition therein, the lowermost portion of the planar screen abutting the partition and communicating with a tilted embryo discharge chute, the receptacle provided with a cover having an opening therein, the opening provided with a hopper extending upwardly therefrom and positioned under the egg cracking and opening mechanism, and a tilted chute positioned adjacent to the egg cracking and opening mechanism for removing the emptied shells.

10. Apparatus according to claim 9 wherein the means operative to produce continual shaking is arranged to shake the screen in a generally horizontal plane.

11. Apparatus according to claim 9 wherein the upper end of the hopper is sufficiently large in the direction of shaking so that it is able to receive the contents at all times during shaking.

* * * * *